United States Patent [19]  [11] 4,075,167
Takamizawa et al.  [45] Feb. 21, 1978

[54] MALEIMIDO GROUP-CONTAINING ORGANOSILICON COMPOUNDS

[75] Inventors: Minoru Takamizawa; Yasushi Yamamoto; Yoshio Inoue, all of Annaka; Atsumi Noshiro, Chiba; Hitoshi Fujii, Tokyo, all of Japan

[73] Assignees: Dai Nippon Printing Co., Ltd.; Shin-Etsu Chemical Co., Ltd., both of Tokyo, Japan

[21] Appl. No.: 644,319

[22] Filed: Dec. 24, 1975

[30] Foreign Application Priority Data
Dec. 28, 1974 Japan .................................. 50-3997

[51] Int. Cl.$^2$ ............................................. C08G 77/04
[52] U.S. Cl. ...................... 260/46.5 E; 260/46.5 UA; 260/295 D; 260/326.5 A; 260/326.5 FM
[58] Field of Search .................... 260/326.5 A, 46.5 E

[56] References Cited
U.S. PATENT DOCUMENTS
3,444,128  5/1969  Wu ...................................... 260/46.5

Primary Examiner—Leonard Schenkman
Attorney, Agent, or Firm—Toren, McGeady and Stanger

[57] ABSTRACT

Novel organosilicon compounds having in a molecule at least one maleimido group bonded to a silicon atom through a Si-C linkage, synthesized by reaction of a derivative of maleic anhydride with an organosilicon compound having an amino-substituted hydrocarbon group bonded to the silicon atom. The reaction proceeds in two steps, the first step being addition of the amino group to the maleic anhydride derivative to form an amide structure and the second step being dehydration of the amide structure to form a maleimido ring. The organosilicon compounds having remarkable photosensitivity can be polymerized and cured on exposure to ultraviolet light, and the cured films are insoluble in organic solvents.

10 Claims, No Drawings

MALEIMIDO GROUP-CONTAINING ORGANOSILICON COMPOUNDS

THE FIELD OF THE INVENTION

This invention relates to novel organosilicon compounds and, in more particular, to novel organosilanes or organopolysiloxanes having one or more maleimido groups, each bonded to a silicon atom through a Si-C linkage in a molecule. The invention further relates to a method for the preparation of the novel organosilicon compounds.

DESCRIPTION OF THE PRIOR ART

In the prior art, various types of photopolymerizable or photocurable organosilicon compounds are known. The photopolymerizability or photocurability of the known organosilicon compounds, however, is not satisfactory when no photosensitizer is contained. In addition, the conventional photosensitizers employed for the purpose are poorly compatible with the organosilicon compounds and, for that reason, such disadvantageous phenomenon as the separation or precipitation of the photosensitizer from its mixture with the photocurable organosilicon compound used to take place.

OBJECTS OF THE INVENTION

In view of the above-described disadvantages in the prior art types of photocurable organosilicon compounds, it is the object of this invention to provide novel organosilicon compounds having improved sensitivity in photopolymerization or photocure without the use of any photosensitizers.

It is another object of the invention to provide a method for preparing the novel photocurable organosilicon compounds.

SUMMARY OF THE INVENTION

In accordance with this invention, the novel organosilicon compounds are organosilanes or organopolysiloxanes represented by the formula

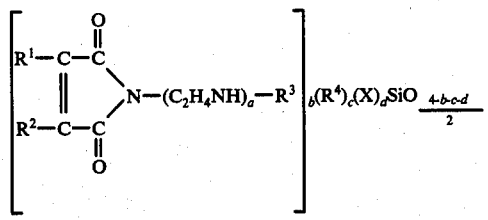

where $R^1$ is a monovalent aromatic or heterocyclic group, $R^2$ is a hydrogen or halogen atom, a cyano group or a monovalent hydrocarbon group with 1 to 4 carbon atoms, $R^3$ is a divalent hydrocarbon group with 1 to 10 carbon atoms, $R^4$ is a monovalent hydrocarbon group, X is a hydroxy group or hydrolyzable atom or group, $a$ is zero or 1, $b$ is a positive number not exceeding 1, and $c$ and $d$ each are zero or positive numbers not exceeding 3 with the proviso that $b+c+d$ is a positive number not exceeding 4.

Further in accordance with the invention, the organosilicon compounds are prepared by reacting a derivative of maleic anhydride represented by the general formula

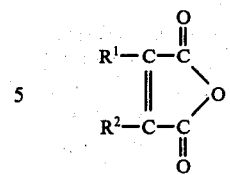

where $R^1$ and $R^2$ each have the same meaning as defined above, with an organosilicon compound expressed by the formula

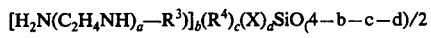

$$[H_2N(C_2H_4NH)_a-R^3)]_b(R^4)_c(X)_dSiO_{(4-b-c-d)/2} \quad (III)$$

where $R^3$, $R^4$, X, $a$, $b$, $c$ and $d$ each have the same meaning as defined above.

DETAILED DESCRIPTION OF THE INVENTION

To describe the novel organosilicon compounds of the present invention in further detail, $R^1$ in formulas (I) and (II) above is a monovalent aromatic group or a monovalent heterocyclic group, such as, an aryl group exemplified by a phenyl, tolyl, xylyl, biphenylyl or naphthyl group, a nitro-, alkoxy- or halogen-substituted derivative thereof, a thioenyl, furyl or pyridyl group or the like, $R^2$ is a hydrogen atom, a halogen atom, a cyano group or a monovalent hydrocarbon group exemplified by a methyl, ethyl, iso-propyl, n-propyl, tert-butyl or n-butyl group, $R^3$ is a divalent hydrocarbon group having 1 to 10 carbon atoms, such as, an alkylene group exemplified by a methylene, ethylene or propylene group, an arylene group exemplified by a phenylene or naphthylene group or an alkarylene group exemplified by a tolylene, xylylene or phenyleneethylene group, $R^4$ is a monovalent hydrocarbon group, such as, an alkyl group exemplified by a methyl, ethyl or propyl group, an aryl group exemplified by a phenyl group, an aralkyl group exemplified by a benzyl or phenylethyl group, an alkaryl group exemplified by a tolyl or ethylphenyl group, an alkenyl group exemplified by a vinyl or allyl group or a cycloalkyl group exemplified by a cyclohexyl group and X is a hydroxy group or a hydrolyzable atom or group, such as, a halogen atom, an alkoxy, acyloxy or aminoxy group or the like.

The molecular structure of the organosilicon compound of the invention may differ widely depending upon the numbers $a$, $b$, $c$ and $d$ in formula (I). For example, when $b+c+d$ is equal to 4, the compound concerned is an organosilane while, when $b+c+d$ is smaller than 4, it is an organopolysiloxane. The molecular configuration of the organopolysiloxane may be a linear, branched or ringed chain, and even a three-dimensionally crosslinked network structure is also possible.

The novel organosilicon compounds of the present invention as expressed by formula (I) is prepared by a method comprising reacting a derivative of maleic anhydride of formula (II) with an organosilicon compound of formula (III).

Several of the examples of the maleic anhydride derivatives represented by formula (II) are phenylmaleic anhydride, tolylmaleic anhydride, α-phenyl-β-methylmaleic anhydride, α-phenyl-β-cyanomaleic anhydride, α-phenyl-β-chloromaleic anhydride, naphthylmaleic anhydride, furylmaleic anhydride, thienylmaleic anhydride, pyridylmaleic anhydride and p-chlorophenylmaleic anhydride.

The organosilicon compound of formula (III), similarly as in the organosilicon compound of formula (I), is an organosilane when b+c+d is equal to 4 or an organopolysiloxane when b+c+d is smaller than 4. Several examples of such organosilanes are 3-aminopropyltrimethylsilane, N-aminoethyl-3-aminopropyltrimethylsilane, 3-aminopropyltriethoxysilane, 3-aminopropylmethyldimethoxysilane, N-aminoethyl-3-aminopropyltrimethoxysilane, N-aminoethyl-3-aminopropylmethyldimethoxysilane and hydroxy-containing silanes in which one or more hydroxy groups are substituted for the alkoxy groups in the above-named alkoxy-containing organosilanes.

The molecular configuration of the organopolysiloxane in conformity with the formula (III) where b+c+d is smaller than 4 may be a linear, branched or ringed chain. Even a three-dimensionally crosslinked network structure is possible depending on the value of b+c+d. Examples of the organopolysiloxane of formula (III) are shown by the following structural or average unit formulas.

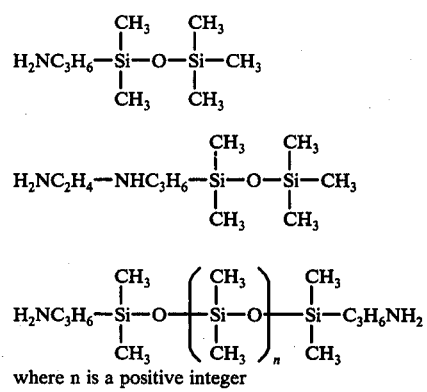

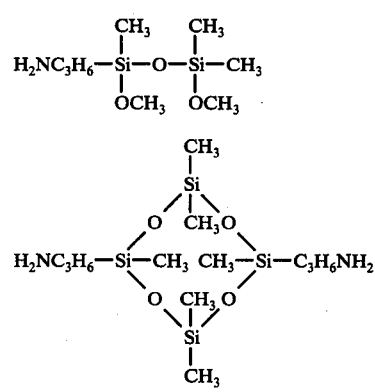

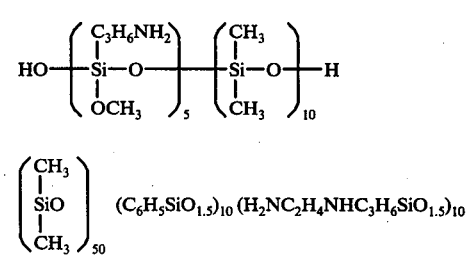

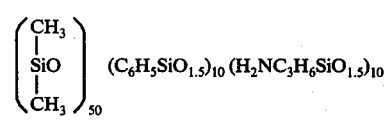

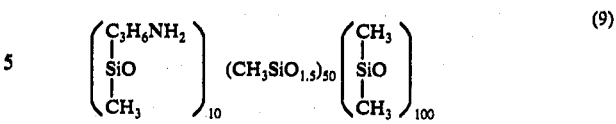

The reaction of the maleic anhydride derivative (II) and the organosilicon compound (III) to form the maleimido group containing organosilicon compound (I) of the invention is carried out in a solution with an appropriate solvent. Solvents suitable for the purpose are exemplified by aromatic hydrocarbon solvents, such as benzene, toluene and xylene and polar organic solvents, such as dimethylformamide, diethylformamide, dimethylsulfoxide, diethylsulfoxide, tetrahydrofuran, dioxane, acetone, methylethylketone and methylisobutylketone. Two or more of these solvents may be employed in combination so that one of the solvents dissolves one of the reactants, e.g., the organosilicon compound (III) and the other solvent or solvents can dissolve the other reactant, i.e., the maleic anhydride derivative (II). Thus the reaction proceeds readily with the reactants dissolved in the solvent or solvents under agitation.

The reaction in accordance with the invention presumably has two steps. The first step is the addition reaction of the maleic anhydride derivative (II) to the terminal amino group of the organosilicon compound (III) to form an amide structure according to the following equation.

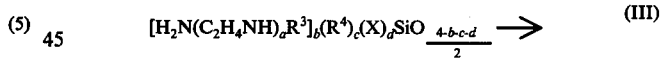

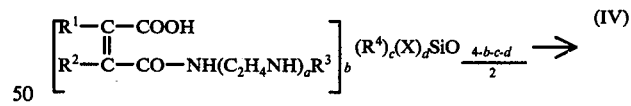

or

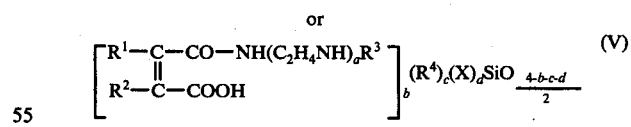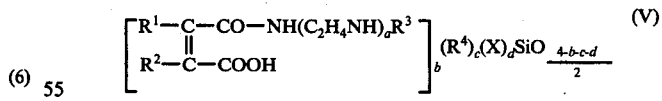

1,670 In the above addition reaction, the formation of compound (IV) or (V) can be evidenced by the appearance of a strong absorption band at around ;b 1,670 cm$^{-1}$ in the infrared absorption spectrum.

The second step is the intramolecular dehydration reaction of the intermediate amide compound (IV) or (V) to form a maleimido ring according to the following equation.

(IV) or (V)

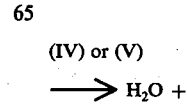 H$_2$O +

-continued

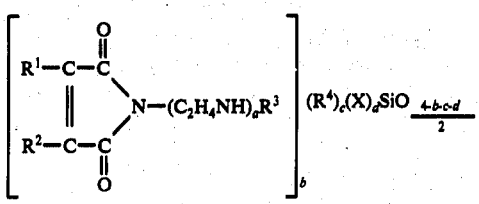

In the above dehydration reaction, the formation of the maleimido ring is supported by the appearance of a strong absorption band at around 1,710 cm$^{-1}$ in the infrared absorption spectrum in parallel with the disappearance of the absorption at 1,670 cm$^{-1}$.

The first step reaction can take place even at relatively low temperatures, for example, 10° to 50° C, while the second step reaction requires a somewhat higher temperature, for example, above 50° C or, preferably, from 100° to 200° C. Therefore, it is advisable that the temperature of the reaction mixture is elevated stepwise. That is to say, the reactants each in a solution are first mixed together conveniently at room temperature under agitation and, after the first step reaction is completed, the reaction mixture is heated to a temperature at which the second step reaction can proceed at a substantial velocity.

The molar ratio of the reactants is preferably in the range such that from 0.1 to 2.0 moles, preferably from 0.8 to 1.5, of the maleic anhydride derivative (II) is employed per mole of the amino groups in the organosilicon compound (III).

The second step reaction, i.e. the intramolecular dehydration involving the formation of the maleimido ring is advantageously accelerated by the catalytic activity of an aliphatic acid anhydride, an aromatic acid anhydride or a tertiary amine. Among the catalysts effective for the reaction, the aliphatic acid anhydrides are exemplified by the anhydrides of acetic acid, propionic acid, butyric acid, valeric acid and the like; the aromatic acid anhydrides are exemplified by the anhydrides of 2-, 3- and 4-toluic acids, 2-, 3- and 4-ethylbenzoic acids, 4-propylbenzoic acid, 4-isopropylbenzoic acid, anisic acid, 2-, 3- and 4-nitrobenzoic acids, isomers of dimethylbenzoic acids, e.g., hemellitic acid, 3,4-xylylic acid and mesitylenic acid, 2,4,6-trimethoxybenzoic acid, α- and β-naphthoic acids, biphenylcarboxylic acids, and the like, and the tertiary amines are exemplified by pyridine, dimethylpyridines, N,N-dimethylaniline, triethylamine, N,N-dimethylbenzylamine and the like. A very small amount, or a catalytic amount of the acid anhydride or the amine is enough to sufficiently accelerate the second step reaction. The acid anhydride or the amine may, on the other hand, be employed as the reaction medium instead of the organic solvents in a large amount without any adverse effects.

The molecular structure of the maleimido group-containing organosilicon compounds (I) of the present invention may differ widely depending on the kinds of the reactants, i.e., the maleic anhydride derivative (II) and the organosilicon compound (III). When an alkoxy-containing organosilane, such as 3-aminopropyltriethoxysilane, is employed as the starting organosilicon compound (III), the resultant maleimido group-containing organosilicon compound (I) is also an alkoxy-containing silane which, as is, can find uses in various applications, subject to modifications with various organopolysiloxanes of linear chain, branched chain or ringed chain structure having one or more hydroxy or alkoxy groups directly bonded to the silicon atoms by dehydration or dealcoholation condensation to give the desired properties, to modified products.

Such a modification reaction of dehydration or dealcoholation condensation is carried out in a suitable organic solvent, for example, an aromatic hydrocarbon solvent, such as toluene or xylene, an aliphatic hydrocarbon solvent, such as n-hexane or n-octane and a polar organic solvent, such as tetrahydrofuran or dimethylformamide, at 50° to 150° C in the presence of a catalyst, such as an organotin compound, organozinc compound or p-toluenesulfonic acid.

The novel maleimido group-containing organosilicon compounds of the invention are readily cured and hardened by the exposure to light, for example, in the ultraviolet range without addition of any photosensitizers, and the cured and hardened films are insoluble in solvents and excellent in chemical resistance, heat stability, weathering resistance, anti-corrosiveness, water-repellency and mold release characteristics.

Further, the maleimido group-containing organosilicon compound of the invention may be in liquid form at room temperature depending on the choice of the starting organosilicon compound (III). Such liquid compounds also exhibit an excellent photocurability without addition of any photosensitizers. Therefore, in the application of the novel compounds of this invention, it is no longer required to add any solvents which have been used to help improve the compatibility of the organosilicon compounds with photosensitizers in the prior art techniques. As the result of such solventless application, problems of pollution in the atmosphere and working environment due to use of solvents will be eliminated.

In photocuring the organosilicon compounds of the invention, it is advisable to add an organic peroxide in order to enhance curing velocity or to lower the temperature at which the photocuring is performed.

By virtue of their excellent properties as described hereinabove, the photocurable organosilicon compounds of this invention can be suitable for various applications including the making of printing plates and photoresists for printed circuits as well as the use as an additive to paints and printing inks.

Following are examples to illustrate the present invention in further detail and not to limit the scope of the invention. In the examples, Me and Ph denote methyl and phenyl group, respectively.

EXAMPLE 1

A mixed solution consisting of 260g of dimethyldichlorosilane and 50g of phenyltrichlorosilane in 1,000g of toluene was added dropwise to 1,100g of water at a temperature not exceeding 25° C to co-hydrolyze the silanes, followed by washing with water, neutralization and dehydration to form a 15% solution of an organopolysiloxane in toluene. Into 1,000g of this organopolysiloxane solution were added 5g of 3-aminopropyltriethoxysilane and 0.2g of dibutyltin dioctoate, and the mixture was subjected to de-ethanolation condensation between the organopolysiloxane and 3-aminopropyltriethoxysilane under reflux for 2 hours resulting to form a toluene solution of an organopolysiloxane with 3-aminopropyl groups expressed by the following formula.

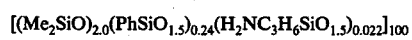

Then, 3.94g of phenylmaleic anhydride, equal to the equimolar amount to the 3-aminopropyl groups, dissolved in 10 ml dimethylformamide was added dropwise at 20° C to the above-obtained toluene solution of the organopolysiloxane, and the reaction was continued at 25° C for 1 hour and thereafter under reflux for 4 hours steadily removing the water produced by the condensation reaction out of the reaction mixture to produce a maleimido group-containing organopolysiloxane expressed by the following formula, as supported by the infrared absorption spectroscopy.

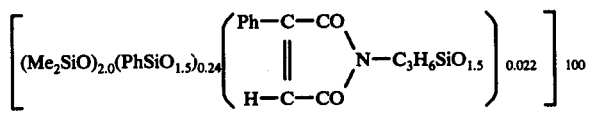

The organopolysiloxane thus produced was a solid at room temperature, its softening point being between 110° to 120° C and the viscosity of its 15% solution in toluene being 8.9 centostokes at 25° C.

An aluminum plate was coated with the toluene solution of the organopolysiloxane, followed by drying to remove toluene resulting in forming film 10μm thick. When exposed to ultraviolet light with an intensity of 110 W/m² for 2 minutes, the coating film was converted into a solvent-insoluble cured film having excellent chemical resistance, heat stability, anticorrosiveness and weathering resistance.

EXAMPLE 2

A solution of 34.8g of phenylmaleic anhydride in 50ml tetrahydrofuran was added dropwise at 20° C to a solution of 98.8g of a 3-aminopropyl group-containing organopolysiloxane expressed by the formula $$H_2NC_3H_6SiMe_2O(Me_2SiO)_{10}SiMe_2C_3H_6NH_2$$

in 100g toluene, and the mixture was subjected to reaction at 25° C for 1 hour and then at 100° to 110° C for 4 hours to produce a maleimido group-containing organopolysiloxane expressed by the following formula.

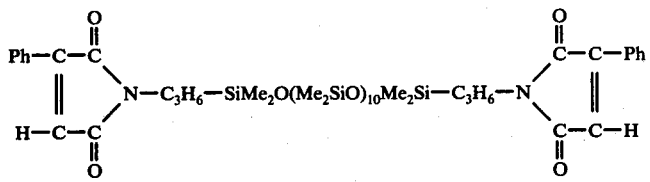

The organopolysiloxane thus produced was a liquid at 25° C, its refractive index being 1.4765 and the viscosity of its 57% solution in toluene being 33.0 centistokes at 25°C.

An aluminum plate was coated with the solution of the product followed by drying to remove toluene. The thus obtained film was exposed to ultraviolet light with an intensity of 110 W/m² for 2 minutes to become a solvent-insoluble cured film having excellent chemical resistance, heat stability, weathering resistance and anti-corrosiveness.

EXAMPLE 3

To a solution of 17.4g of phenylmaleic anhydride in 100g of toluene was added dropwise 22.1g of 3-aminopropyltriethoxysilane at room temperature and, after 1 hour of the reaction at 25° C, the reaction mixture was heated under reflux for 3 hours to give a reaction product of mixed organopolysiloxanes having maleimido groups each expressed by the following formula.

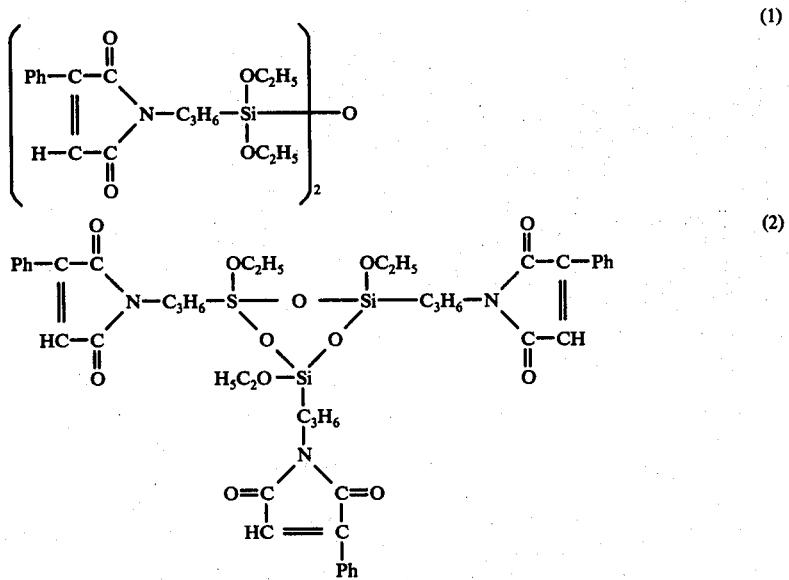

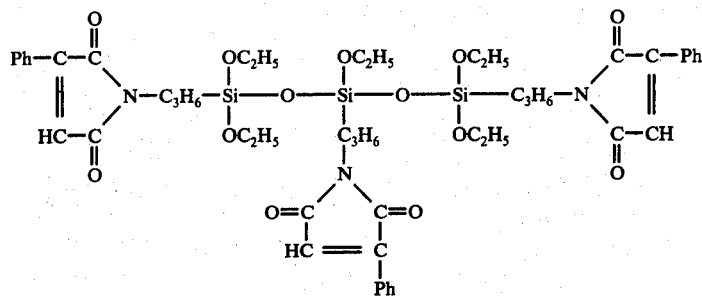

The product was solid at room temperature, its melting point being in the range from 64° to 65° C.

EXAMPLE 4

A mixture of 100g of the maleimido group-containing organopolysiloxane obtained in Example 3 and 150g of a hydroxy-terminated dimethylpolysiloxane expressed by the formula $HO\text{-}(Me_2Si\text{-}O)_{20}H$ was subjected to de-ethanolation reaction to produce an organopolysiloxane expressed by the following average unit formula.

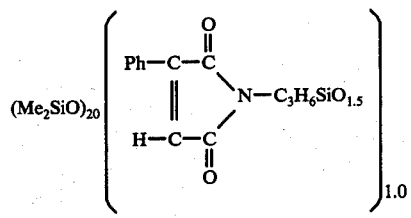

The product was a liquid at 25° C, its refractive index being 1.4182 and the viscosity of its 75% solution in toluene being 13.2 centistokes at 25° C.

An aluminum plate was coated with the toluene solution of the organopolysiloxane, followed by drying to remove the toluene. The resulting coating film was exposed to ultraviolet light with an intensity of 110 W/m² for 2 minutes to form a solvent-insoluble cured film having excellent chemical resistance, heat stability, weathering resistance and anti-corrosiveness.

EXAMPLE 5

To 194g of a 20% solution in toluene of the hydrolyzate of phenyltrichlorosilane were added dropwise 743g of 20% solution of a dimethylpolysiloxane having a polymerization degree about 200 terminated at both chain ends with chlorine atoms and 236g of pyridine. After 1 hour of agitation during which dehydrochlorination reaction took place, pyridine hydrochloride and excessive pyridine were removed by washing with water, followed by dehydration to produce a solution of a copolymerized organopolysiloxane with a 20% by weight concentration.

Into the solution above obtained were added a toluene solution of the maleimido group-containing organopolysiloxane obtained in Example 3 in an amount of 20g as siloxane and 0.1g of dibutyltin dioctoate, and the resulting mixture was heated under reflux for 5 hours to cause reaction. The product thus obtained was a maleimido group-containing organopolysiloxane expressed by the following average unit formula.

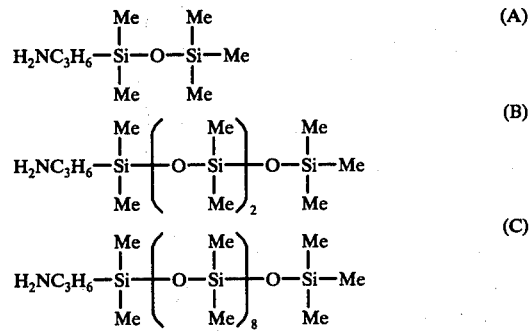

This product was a solid having a softening point in the range from 90° to 100° C. The viscosity of its 20% solution in toluene was 18.3 centistokes at 25° C.

An aluminum plate was coated with a solution of the above product in toluene, followed by drying to remove toluene. The resulting film was exposed to ultraviolet light with an intensity of 110 W/m² for 2 minutes to form a solvent-insoluble cured film having excellent heat stability, chemical resistance, weathering resistance and anti-corrosiveness.

EXAMPLE 6

A 15% solution of 3.46g of phenylmaleic anhydride in dimethylformamide was added dropwise under agitation to a 15% solution in toluene of an equimolar amount of each of the following three amino-containing organopolysiloxanes (A), (B) and (C).

$$H_2NC_3H_6-\underset{\underset{Me}{|}}{\overset{\overset{Me}{|}}{Si}}-O-\underset{\underset{Me}{|}}{\overset{\overset{Me}{|}}{Si}}-Me \quad (A)$$

$$H_2NC_3H_6-\underset{\underset{Me}{|}}{\overset{\overset{Me}{|}}{Si}}\left(-O-\underset{\underset{Me}{|}}{\overset{\overset{Me}{|}}{Si}}\right)_2-O-\underset{\underset{Me}{|}}{\overset{\overset{Me}{|}}{Si}}-Me \quad (B)$$

$$H_2NC_3H_6-\underset{\underset{Me}{|}}{\overset{\overset{Me}{|}}{Si}}\left(-O-\underset{\underset{Me}{|}}{\overset{\overset{Me}{|}}{Si}}\right)_8-O-\underset{\underset{Me}{|}}{\overset{\overset{Me}{|}}{Si}}-Me \quad (C)$$

The reaction was conducted first at 25° C for 1 hour and then under reflux for 4 hours, followed by the removal of the solvents under reduced pressure to give a product of which the formation of the maleimido ring was evidenced by the infrared absorption spectroscopy. The products, their respective softening points in °C and refractive indices (at 25° C) as well as the results of elementary analysis are shwon in the following table. In the table, softening point is abbreviated to S.P. and refractive index is abbreviated to R.I., while the products are expressed by (A'), (B') and (C') each having a molecular formula as mentioned thereunder.

| Siloxane | Product | S.P. | R.I. | | Elementary Analysis, % | | | |
|---|---|---|---|---|---|---|---|---|
| | | | | | C | H | N | Si |
| (A) | (A') | 22–24 | 1.5160 | Calc. | 59.79 | 7.53 | 3.87 | 15.53 |
| | | | | Found | 60.1 | 7.3 | 2.81 | 15.6 |
| (B) | (B') | 19–21 | 1.5040 | Calc. | 51.82 | 7.71 | 2.75 | 22.03 |
| | | | | Found | 52.0 | 7.8 | 2.90 | 22.1 |
| (C) | (C') | 13–15 | 1.4635 | Calc. | 42.77 | 7.92 | 1.47 | 29.41 |
| | | | | Found | 43.0 | 7.7 | 1.3 | 29.4 |

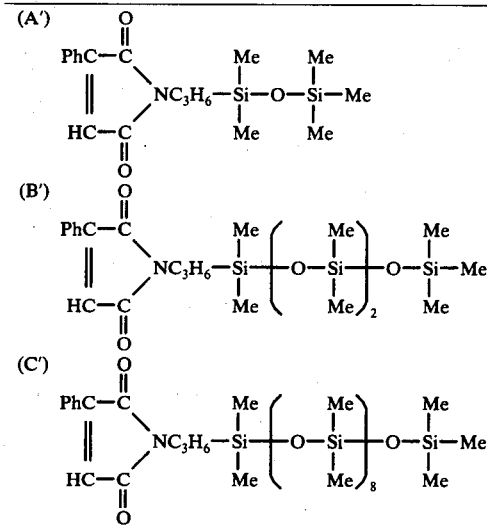

EXAMPLE 7

Reactions were undertaken using the under-mentioned combinations (A) to (I) of maleic anhydride derivatives and amino-containing organopolysiloxanes under reaction conditions similar to those in Example 1 except that each maleic anhydride derivative in an amount specified was dissolved in 20ml of dimethylformamide, while the amount of each amino-containing organopolysiloxane used was 1,000g as a 15% solution in toluene.

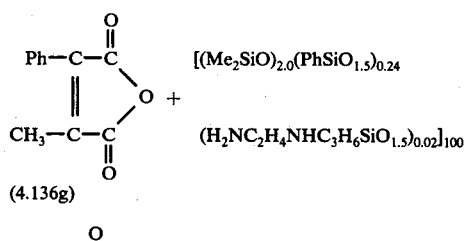

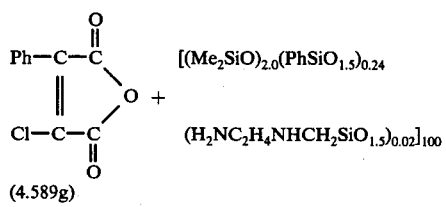

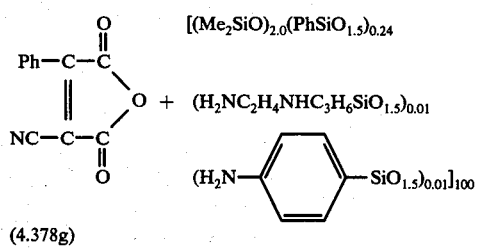

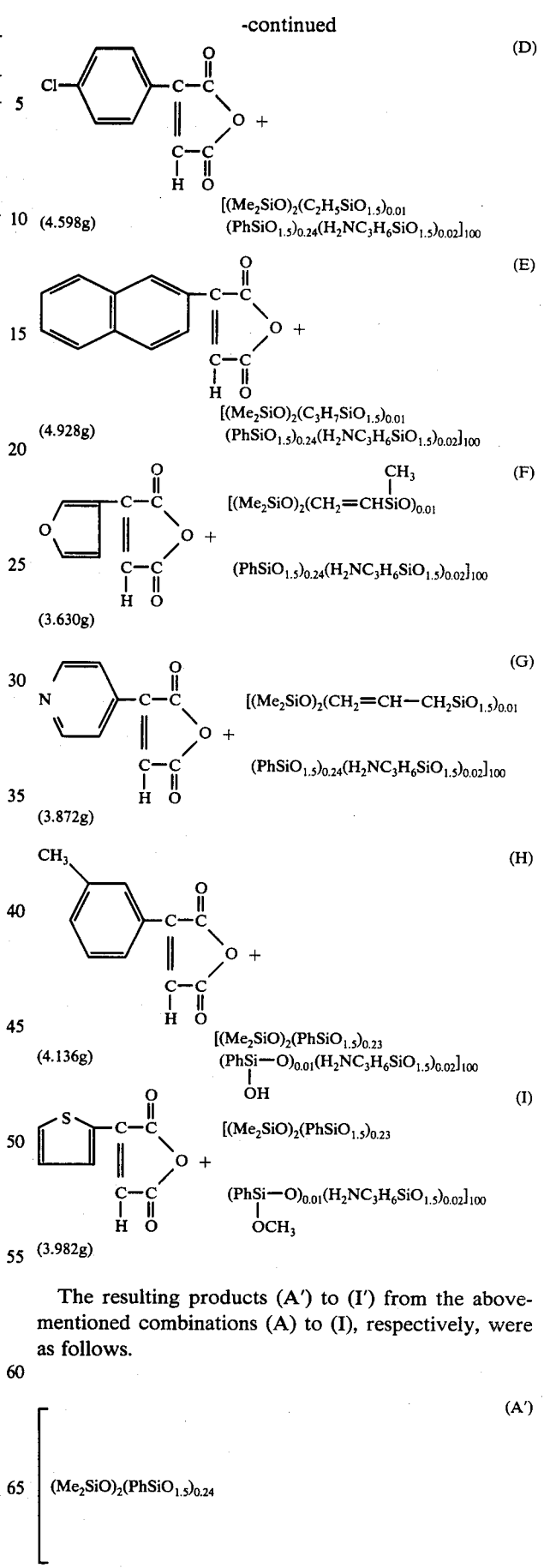

The resulting products (A') to (I') from the above-mentioned combinations (A) to (I), respectively, were as follows.

(A')

$[(Me_2SiO)_2(PhSiO_{1.5})_{0.24}$

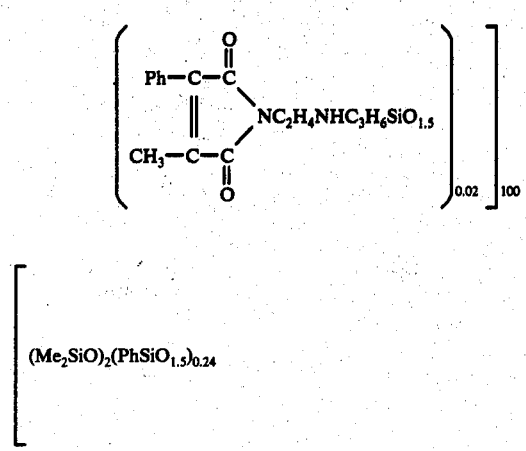
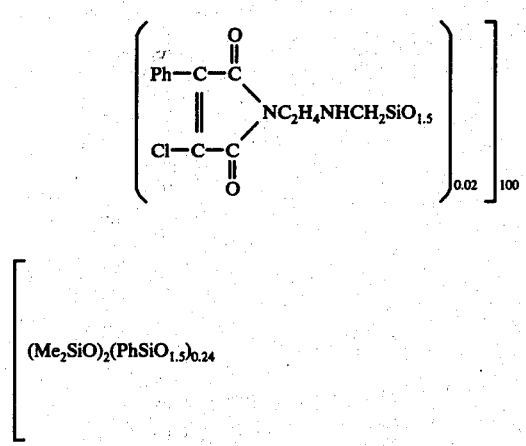
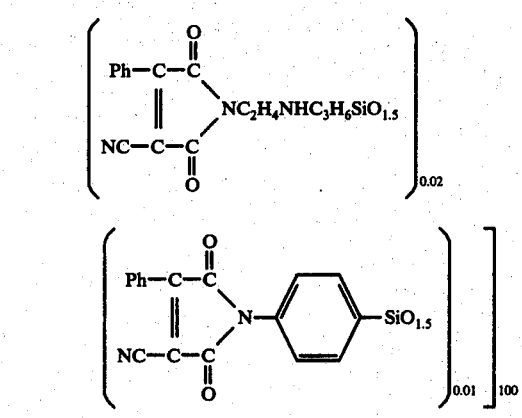
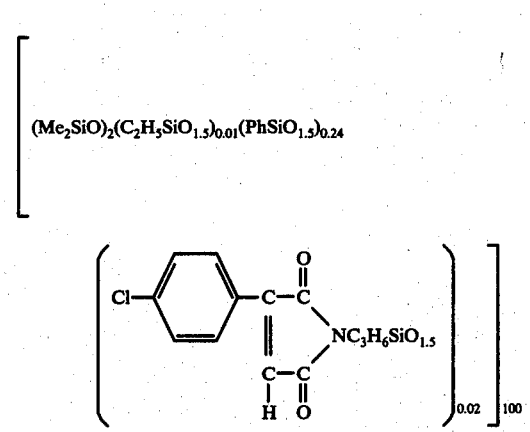
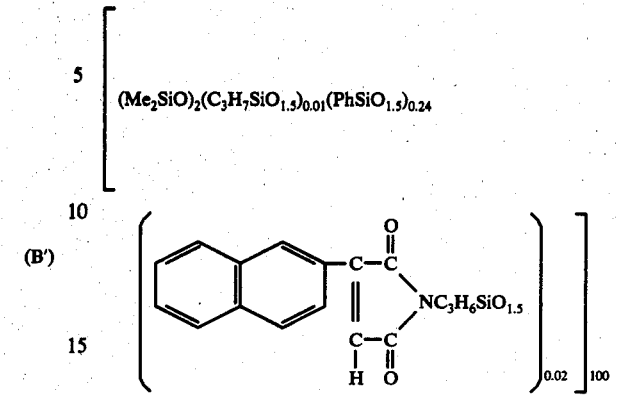
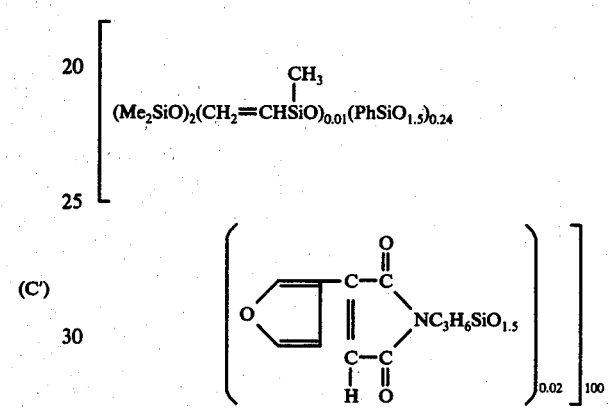
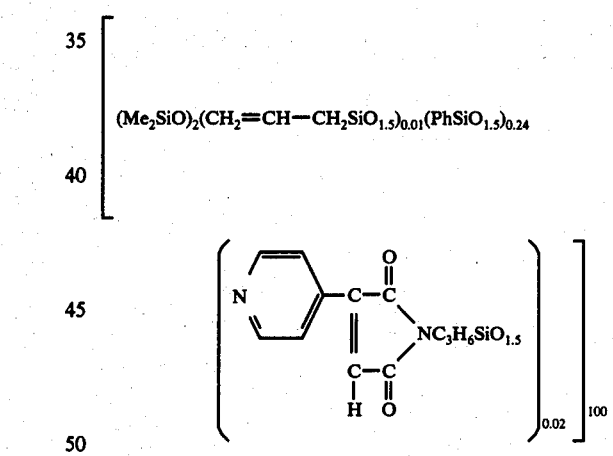
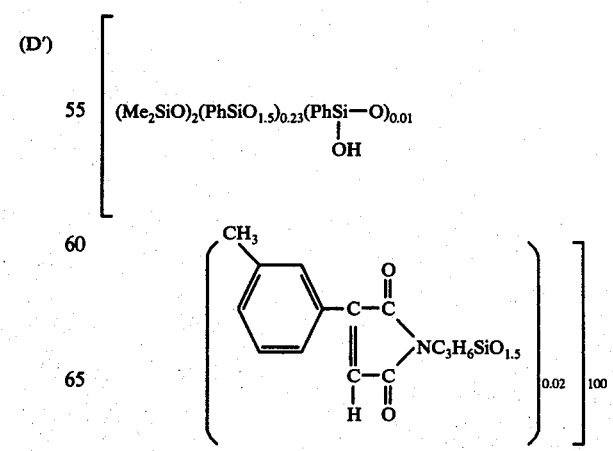

-continued

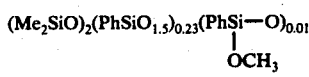

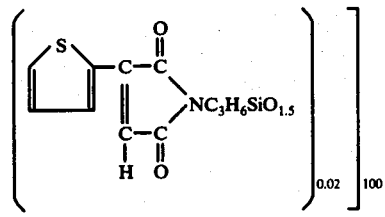

The infrared absorption spectra of these products supported the formation of the maleimido raings. The photocuring tests for the products were carried out as in Example 1 to prove that each product had a good photosensitivity to ultraviolet light.

What is claimed is:

1. An organosilicon compound represented by the formula

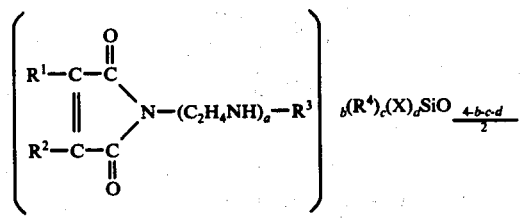 (I')

wherein $R^1$ is a monovalent aromatic group selected from the group consisting of phenyl, naphthyl and substituted phenyl, $R^2$ is hydrogen, chlorine, cyano or methyl, $R^3$ is phenylene or lower alkylene, $R^4$ is a monovalent hydrocarbon group selected from the group consisting of methyl, ethyl, propyl phenyl, benzyl, phenylethyl, tolyl, ethylphenyl, vinyl, allyl and cyclohexyl, X is selected from the group consisting of hydroxy, halogen, alkoxy, acyloxy and aminoxy $a$ is zero or 1, $b$ is a positive number not exceeding 1, and $c$ and $d$ each are zero or positive numbers not exceeding 3 with the proviso that $b+c+d$ is a positive number not exceeding 4.

2. The organosilicon compound as claimed in claim 1 wherein $b+c+d$ is equal to 4.

3. The organosilicon compound as claimed in claim 1 wherein $b+c+d$ is smaller than 4.

4. The organosilicon compound as claimed in claim 1 wherein said monovalent aromatic group denoted by $R^1$ is selected from the class consisting of phenyl, tolyl, naphthyl and their halogen substituted derivatives.

5. The organosilicon compound as claimed in claim 1 wherein $R^2$ is a methyl group.

6. The organosilicon compound as claimed in claim 1 wherein $R^3$ is an alkylene group.

7. The organosilicon compound as claimed in claim 6 wherein said alkylene group is a propylene group.

8. The organosilicon compound as claimed in claim 1 wherein said monovalent hydrocarbon group denoted by $R^4$ is selected from the class consisting of methyl, ethyl, propyl, vinyl, allyl and phenyl groups.

9. The organosilicon compound as claimed in claim 1 wherein said hydrolyzable group denoted by X is an alkoxy group.

10. The organosilicon compound as claimed in claim 9 wherein said alkoxy group is a methoxy group.

* * * * *